United States Patent
Spreiter et al.

(10) Patent No.: US 11,350,976 B2
(45) Date of Patent: Jun. 7, 2022

(54) SYSTEM AND METHOD FOR TREATING A BONE

(71) Applicant: DEPUY SYNTHES PRODUCTS, INC., Raynham, MA (US)

(72) Inventors: Gregor Spreiter, Zuchwil (CH); Henri Défossez, Neuchatel (CH); Simon Scherrer, Zurich (CH)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 198 days.

(21) Appl. No.: 16/675,863

(22) Filed: Nov. 6, 2019

(65) Prior Publication Data

US 2021/0128213 A1    May 6, 2021

(51) Int. Cl.
| A61B 17/72 | (2006.01) |
| A61B 17/86 | (2006.01) |
| A61B 17/88 | (2006.01) |

(52) U.S. Cl.
CPC ...... *A61B 17/8665* (2013.01); *A61B 17/7233* (2013.01); *A61B 17/7225* (2013.01)

(58) Field of Classification Search
CPC ........... A61B 17/8665; A61B 17/7233; A61B 17/7225; A61B 17/725; F16B 37/125; F16B 37/127
USPC ......... 606/64, 301, 304, 308, 311, 315, 316, 606/323; 411/178
See application file for complete search history.

(56) References Cited

U.S. PATENT DOCUMENTS

| 4,760,843 | A | * | 8/1988 | Fischer | A61B 17/686 411/178 |
| 5,217,462 | A | * | 6/1993 | Asnis | A61B 17/74 606/105 |
| 6,524,314 | B1 | * | 2/2003 | Dean | A61B 17/72 606/64 |
| 6,565,573 | B1 | * | 5/2003 | Ferrante | A61B 17/863 606/308 |
| 7,578,825 | B2 | * | 8/2009 | Huebner | A61B 17/683 606/104 |
| 2009/0228049 | A1 | * | 9/2009 | Park | A61B 17/8897 606/301 |
| 2009/0326533 | A1 | * | 12/2009 | Dell'Oca | A61B 17/8645 606/64 |
| 2014/0094860 | A1 | * | 4/2014 | Reimels | A61B 17/8685 606/323 |
| 2016/0081727 | A1 | * | 3/2016 | Munday | A61B 17/7225 606/62 |
| 2016/0256207 | A1 | * | 9/2016 | Zander | A61B 17/683 |

(Continued)

*Primary Examiner* — Eduardo C Robert
*Assistant Examiner* — David C Comstock
(74) *Attorney, Agent, or Firm* — Fay Kaplun & Marcin, LLP

(57) ABSTRACT

A nut for treating a bone includes a head and a body extending longitudinally from the head to a free end and including a channel extending longitudinally thereinto from the free end, the channel configured to engage an end of a bone screw, and an exterior threading extending about the body from an exterior surface thereof along an entire length thereof, an outer contour of the exterior threading defined via radially outermost edges of the exterior threading, a first portion of the outer contour adjacent the head portion having a smaller diameter than a second portion of the outer contour extending from the first portion to the free end of the body.

21 Claims, 4 Drawing Sheets

(56) References Cited

U.S. PATENT DOCUMENTS

2017/0105774 A1\* 4/2017 Prien .................... A61B 17/861
2018/0368894 A1\* 12/2018 Wieland ............... A61B 17/863

\* cited by examiner

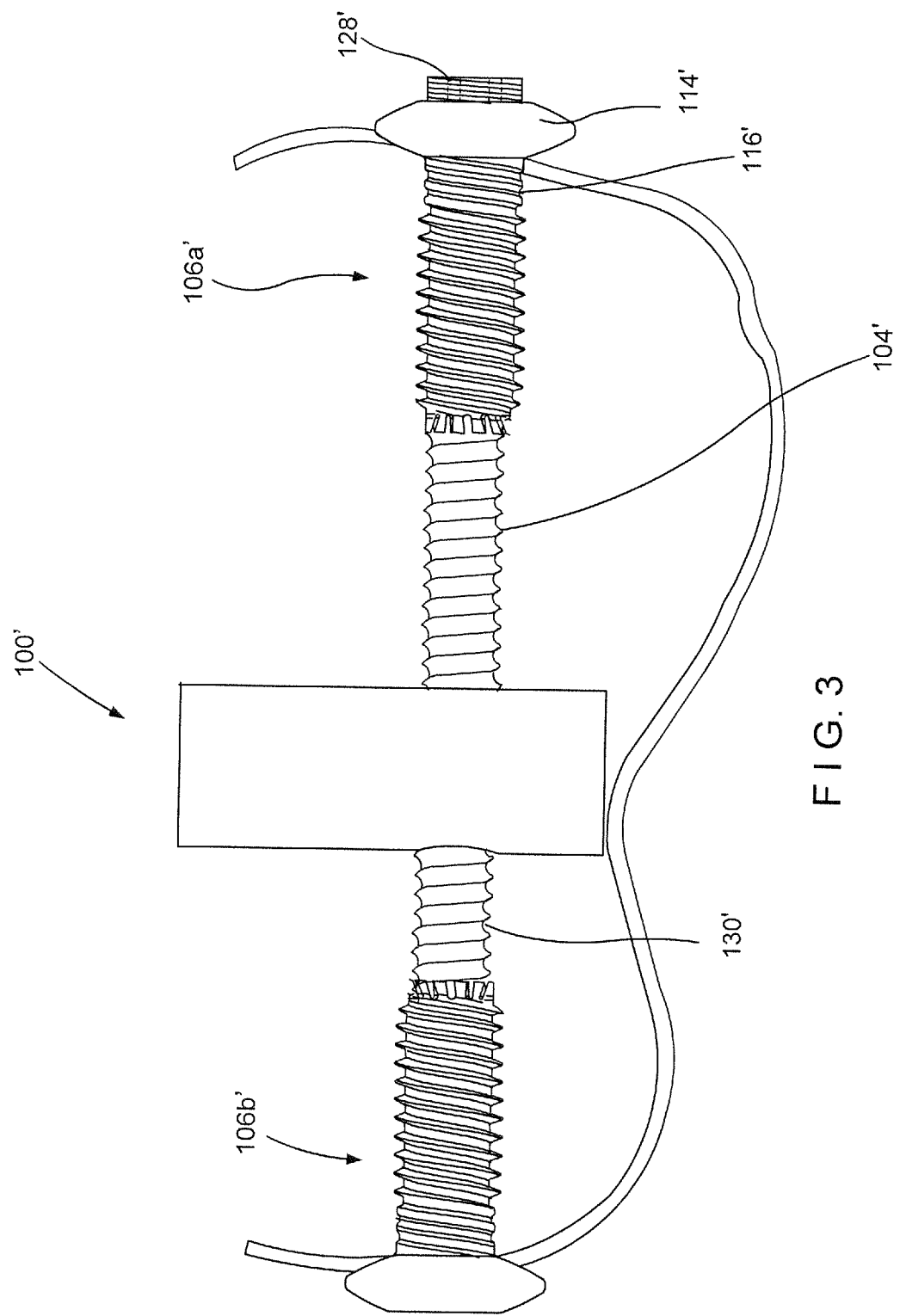

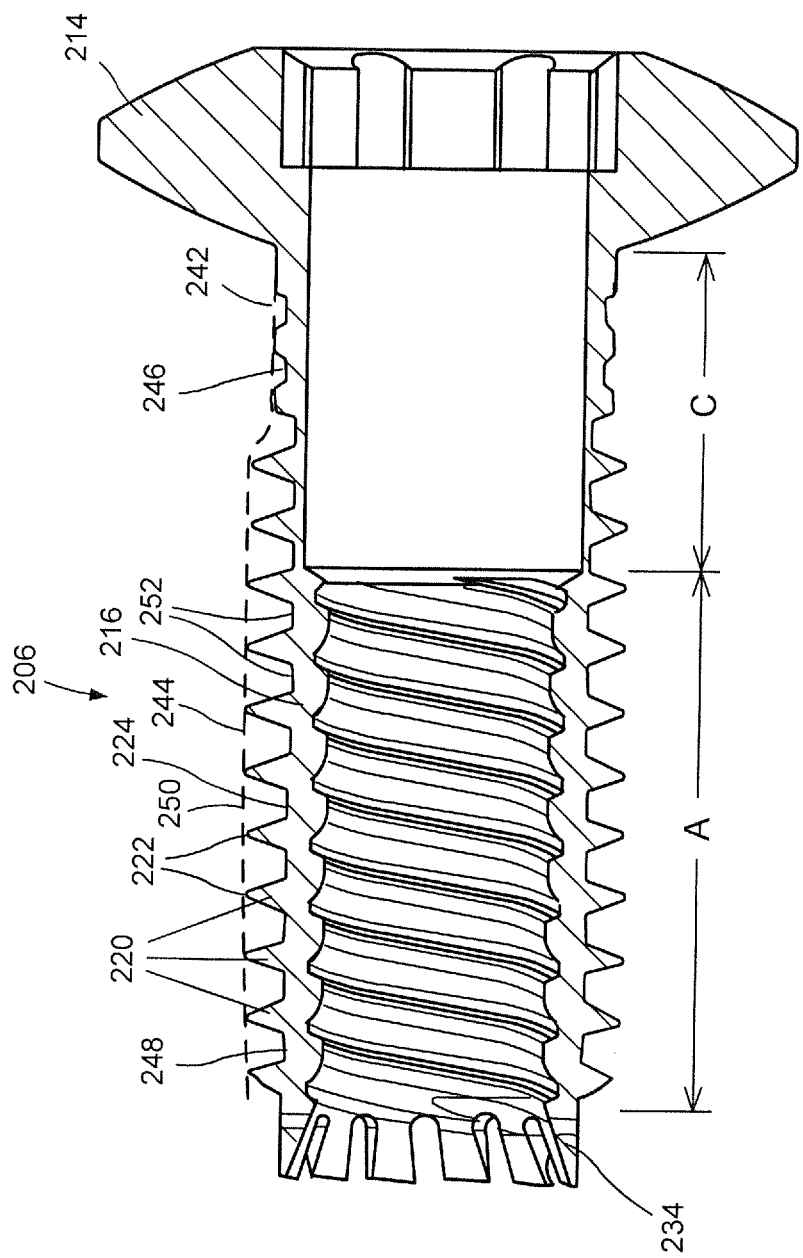

SYSTEM AND METHOD FOR TREATING A BONE

BACKGROUND

A fracture of a long bone such as, for example, a femur, may be treated using an intramedullary nail inserted into a medullary canal of the bone after the fracture has been reduced. In some cases, particularly for distal condylar fractures, the bone may be treated using a retrograde nail, insertable into the medullary canal from a distal end of the bone. Locking screws may be inserted through the bone into locking holes extending transversely through the intramedullary nail to fix the intramedullary nail to the bone and/or to provide additional stability to the bone.

SUMMARY

The present disclosure relates to a nut for treating a bone, comprising a head and a body extending longitudinally from the head to a free end and including a channel extending longitudinally thereinto from the free end, the channel configured to engage an end of a bone screw, and an exterior threading extending about the body from an exterior surface thereof along an entire length thereof, an outer contour of the exterior threading defined via radially outermost edges of the exterior threading, a first portion of the outer contour adjacent the head portion having a smaller diameter than a second portion of the outer contour extending from the first portion to the free end of the body.

The present disclosure also relates to a system for treating a long bone, comprising an intramedullary nail insertable through a medullary canal of a bone, the intramedullary nail extending from a proximal end to a distal end and including a locking hole extending through the intramedullary nail along an axis extending at an angle relative to a longitudinal axis of the intramedullary nail, a locking screw configured to be inserted into the bone and through the locking hole, the locking screw including a head portion and a shaft extending therefrom to a free end, the shaft including a threading extending therealong, and a nut configured to be inserted into bone, the nut including a head and a body extending therefrom to a free end, the body including a channel extending longitudinally thereinto from the free end, the channel configured to threadedly engage the free end of the locking screw, an exterior threading extending about the body from an exterior surface thereof along an entire length thereof, an outer contour of the exterior threading defined via radially outermost edges of the exterior threading, a first portion of the outer contour adjacent the head portion having a smaller diameter than a second portion of the outer contour extending from the first portion to the free end of the body.

The present disclosure also relates to a method for treating a bone, comprising inserting an intramedullary nail into a medullary canal of a femur through an insertion point at a distal end of the femur, driving a locking screw through a first side of the femur so that a shaft of the locking screw extends through a locking hole extending through a distal portion of the intramedullary nail along an axis angled with respect to a longitudinal axis of the intramedullary nail and a head portion of the locking screw contacts a cortex along the first side of the femur, and inserting a nut through a second side of the femur opposite the first side of the femur so that a free end of the shaft of the locking screw is threadedly received within a channel of the nut, the nut including a head and a body portion extending from the head to a free end, the channel extending longitudinally into the body from the free end, an exterior threading extending about the body from an exterior surface thereof along an entire length thereof, an outer contour of the exterior threading defined via radially outermost edges of the exterior threading, a first portion of the outer contour adjacent the head portion having a smaller diameter than a second portion of the outer contour extending from the first portion to the free end of the body so that, as the nut is inserted through the bone to engage the locking screw, the nut rotates to align the channel with the threading of the locking screw.

BRIEF DESCRIPTION

FIG. 3 shows a longitudinal side view of a portion of a system according to another exemplary embodiment of the present disclosure;

FIG. 4 shows a longitudinal cross-sectional view of a nut according to another exemplary embodiment of the present disclosure.

DETAILED DESCRIPTION

Figure 1:
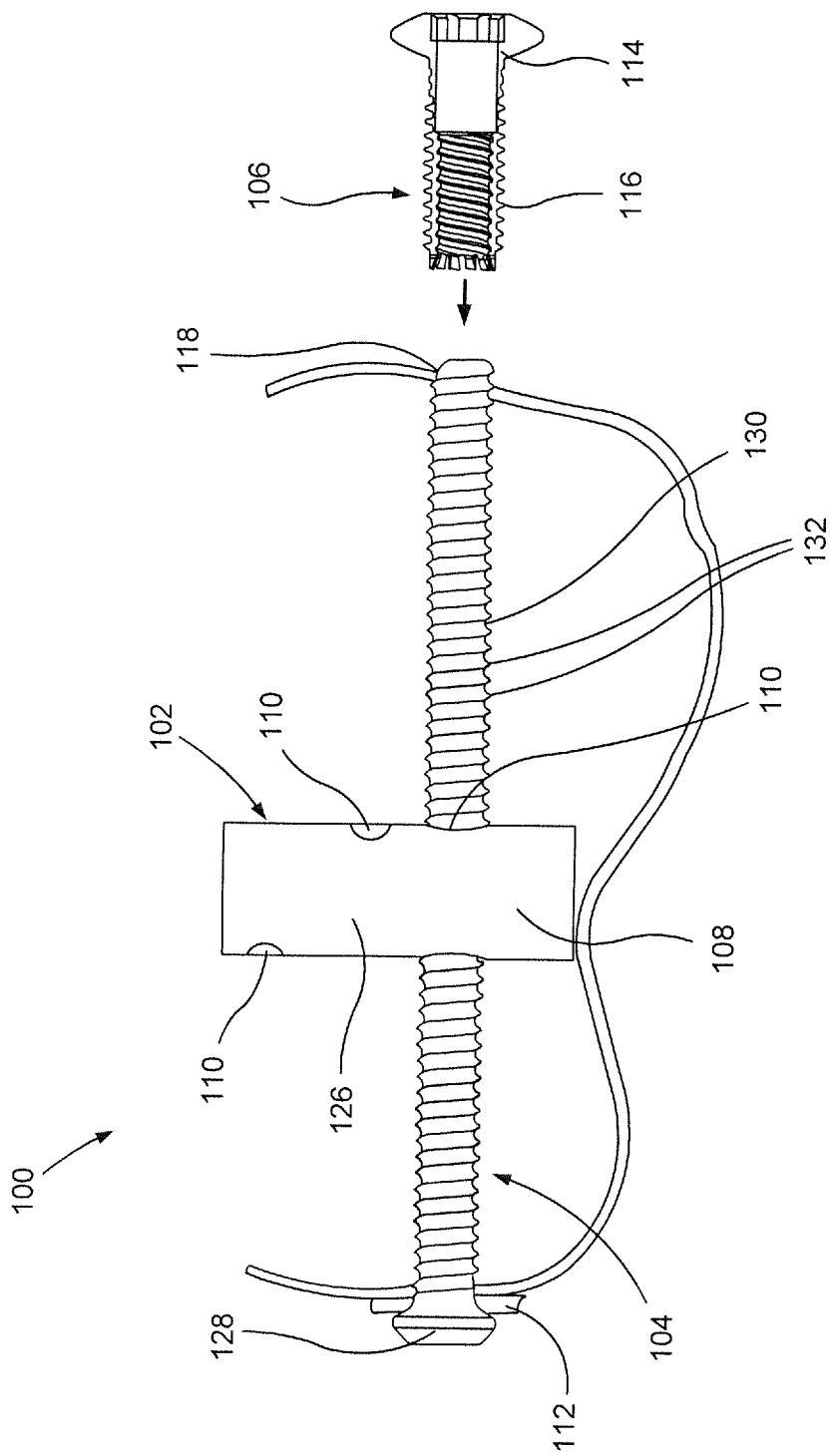
FIG. 1 shows a longitudinal side view of a portion of a system according to an exemplary embodiment of the present disclosure.

The present disclosure may be understood with reference to the following description and the appended drawings, wherein like elements are referred to with the same reference numerals. The present embodiments relate to the treatment of bone and, in particular, relates to the treatment of long bones. Exemplary embodiments describe a system comprising an intramedullary nail configured to be inserted through a medullary canal of a long bone (e.g., femur) in combination with a locking screw insertable through a locking hole extending transversely through the intramedullary nail and a nut configured to engage a threaded end of the locking screw. The locking screw and nut together act to provide additional stability, fixation and/or compression at, for example, a distal end of the bone.

Exemplary embodiments describe a nut including a head portion and a body portion including a channel configured to threadedly receive the threaded end of the locking screw. The nut of this embodiment also includes an exterior threading along an outer surface of the body. An outer contour of the nut, defined via radially outermost edges of the exterior threading, narrows toward the head portion so that the nut may be rotated to align the threading of the channel with the locking screw. A core diameter, defined as a diameter of a radially inner-most portion of the exterior surface of the body portion (i.e., the portion of the exterior surface from which the exterior threading projects radially outward) increases toward the head portion of the nut to provide stability at the cortex when the nut is fully inserted. Although the exemplary embodiments specifically show and describe a retrograde femoral nail system, it will be understood by those of skill in the art that the system of the present disclosure may be used to treat any of a variety of long bones such as, for example, the humerus regardless of the direction of approach. Additionally, although the exemplary embodiments show and describe the locking screw and nut as providing stability and/or compression for the distal end of the bone, it will be understood by those of skill in the art that the locking screw and nut may be used to provide additional stability/compression across any portion of the bone. It should be noted that the terms proximal and distal, as used herein, are intended to refer to a direction corresponding to proximal and distal ends of a bone, respectively, with distal referring to a direction away from a point of attachment to the core of the body and proximal toward this point of attachment as would be understood by those of skill in the art.

Figure 2:
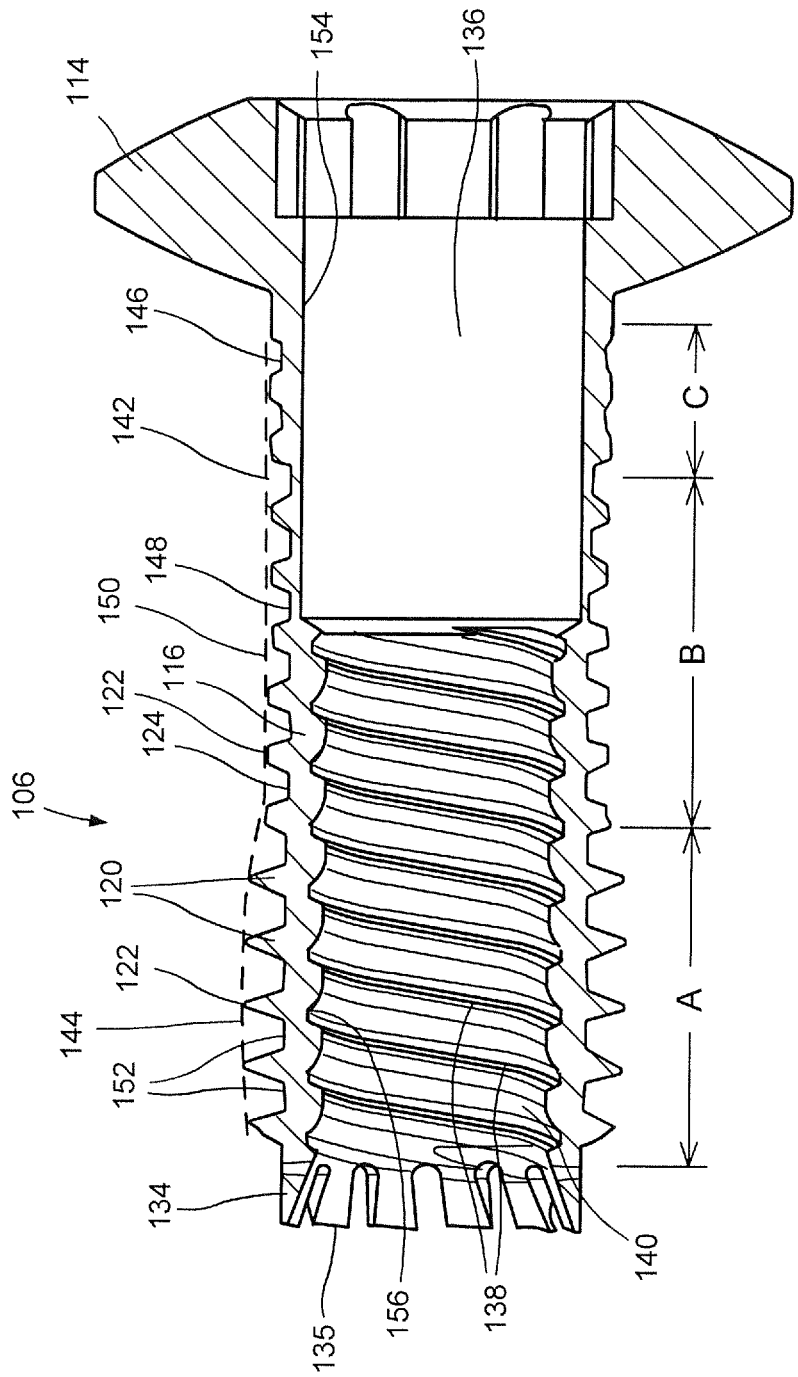
FIG. 2 shows a longitudinal cross-sectional view of a nut according to the system of FIG. 1.

As shown in FIGS. 1 and 2, a system 100 according to an exemplary embodiment of the present disclosure comprises an intramedullary nail 102 configured to be inserted through a medullary canal of a long bone (e.g., femur) along with a locking screw 104 and a nut 106 for securing, for example, a distal end 108 of the intramedullary nail 102 relative to the bone to provide stability and/or compression across a fracture of the bone. The locking screw 104 is configured to be inserted through a locking hole 110 extending transversely through a portion of the intramedullary nail 102 from a first side of the bone.

The nut 106 includes a head 114 and a body 116 extending therefrom, the body 116 configured to engage a free end 118 of the locking screw 104 from a second side of the bone, opposite the first side to provide additional stability, fixation and/or compression of a portion of the bone through which the locking screw 104 extends. The body 116 includes an exterior threading 120 extending radially outward along all or a portion of a length of an exterior surface 124 thereof. An outer contour 150 of the body 116 defined by radially outermost edges 122 of the exterior threading 120, narrows along a portion of the body 116 adjacent to the head 114 to facilitate alignment with the locking screw 104 as the nut 106 is rotated about a longitudinal axis of the locking screw 104.

Additionally, a core diameter—a diameter defined as a diameter of the body 116 defined at radially inner-most points 152 on the exterior surface 124 (i.e., the points from which the exterior threading 120 extend radially outward)—is larger adjacent to the head 114 so that, the nut 106 provides stability at the cortex along the second side when the body 116 of the nut 106 is fully inserted into the bone. Although the core diameter is larger adjacent to the head 114, it will be understood by those of skill in the art that cracking of the cortex along the second side of the bone is avoided as the increase in the core diameter is compensated for by a reduction on the outer contour 150 adjacent to the head 114.

The intramedullary nail 102 extends from the distal end 108 to a proximal end (not shown). In one exemplary embodiment, the intramedullary nail 102 is a retrograde femoral nail configured to be inserted into the medullary canal of a femur via an insertion point at a distal end of the bone. The intramedullary nail 102 in this embodiment is sized, shaped and configured to correspond to a size and shape of the medullary canal of the target bone. In this embodiment, the locking hole 110 extends transversely through a distal portion 126 of the nail 102 and is configured to receive the locking screw 104 therethrough to, for example, provide stability across the distal end of the femur.

The locking hole 110 extends through the distal portion along an axis angled with respect to a longitudinal axis of the nail 102. In one embodiment, the locking hole 110 extends through the distal portion 126 along an axis substantially perpendicular to the longitudinal axis of the of the nail 102. In another embodiment, the locking hole 110 extends through the distal portion 126 along an axis that is non-perpendicularly angled with respect to the longitudinal axis of the nail 102. Although the exemplary embodiments describe a single locking hole 110, it will be understood by those of skill in the art that the intramedullary nail 102 may include more than one locking hole 110, each configured to receive a locking screw 104 therethrough.

The locking screw 104 may be a standard bone screw, as will be understood by those of skill in the art, including a head portion 128 and a shaft 130 extending therefrom to the free end 118. The shaft 130 includes a threading 132 along an outer surface thereof so that the locking screw 104 may be inserted into the bone and through the locking hole 110 via a rotation of the locking screw 104 about a longitudinal axis thereof. As will be understood by those of skill in the art, the locking screw 104 may be driven into the bone using a driver that is, for example, engageable with a driving recess within the head portion 128. As would be understood by those skilled in the art, the driver and the driving recess may be correspondingly sized and shaped so that, when engaged, rotation of the driver correspondingly rotates the locking screw 104 to drive the locking screw 104 into the bone. The locking screw 104 is insertable into the bone and through the locking hole 110 so that, when fully inserted, the head portion 104 abuts a cortex of the bone along the first side of the bone. In one embodiment, a length of the locking screw 104 is selected so that upon full insertion into the bone, the free end 118 of the shaft 130 protrudes from the far cortex by approximately 2 mm.

As described above, the nut 106 includes the head 114 and body 116 extending therefrom to a free end 134 configured to surround and engage the free end 118 of the locking screw 104. Similarly to the locking screw 104, the head 114 of the nut 106 includes a driving recess engageable with a driver for driving (i.e., rotating) the nut 106 into the bone. The free end 134 may include a cutting edge 135 configured to facilitate insertion of the nut 106 through the cortex of the bone. The body 116 includes a channel 136 extending longitudinally thereinto from the free end 134. The channel 136 is configured to receive the free end 118 of the locking screw 104 therein and includes an interior threading 138 along an interior surface 140 thereof, which is sized and pitched to correspond to the threading 132 of the locking screw 104 to threadedly engage the threading 132 of the locking screw 104. In one embodiment, a portion 154 of the channel 136 extending through the body 116 adjacent the head 114 may have a larger diameter than a remaining portion 156 of the channel 136 extending through the body 116. According to one example, the threading 138 may extend along the remaining portion 156 such that the larger diameter portion 154 is thread free. In another embodiment, the threading 138 may extend along an entire length of the channel 136. In another embodiment, a diameter of the channel 136 may be constant along an entire length thereof.

As described above, the body 116 of the nut 106 in this embodiment includes exterior threading 120 on the exterior surface 124 along an entire length of the body 116. Thus, when the nut 106 is driven into the bone, the exterior threading 120 engages the bone. In particular, the nut 106 may be driven into the second side of the bone opposite the first side, so that a longitudinal axis of the nut 106 is in substantial alignment with the longitudinal axis of the locking screw 104 that has been inserted through the locking hole so that, as the nut 106 is driven into the bone, the body 116 is threaded over the free end 118 of the locking screw 104.

The outer contour 150 (shown via a dotted line in FIG. 2) of the nut 106, which is defined via the radially outermost edges 122 of the exterior threading 120, narrows toward the head 114. In other words, a diameter of the outer contour 150 along a first portion 142 of the body 116 adjacent the head 114 is smaller than a diameter of the outer contour 150 along a second portion 144 of the body 116 extending from the first portion 142 to the free end 134. Since the outer contour 150 of the nut 106 (a path defined by the radially outermost points on the exterior threading 120) along the first portion 142 proximate the head 114 defines a diameter smaller than the diameter of the outer contour 150 in the second portion 144, the interior threading 138 of the channel 136 aligns with the threading 132 of the locking screw 104 as the nut 106 is rotated into the bone. In other words, as the first part of the outer contour 150 of the nut 106 penetrates the bone it cuts a path slightly wider than the second portion 144 with this slightly increased diameter allows for slight movement of the nut 106 relative to an axis of insertion enabling the nut 106 to adjust position to more accurately align the axis of the channel 136 of the nut 106 with the axis of the shaft 130 of the locking screw 104.

The core diameter of the exterior surface 124 of the body 116, along which the exterior threading 120 extends, also varies along a length thereof. The core diameter is defined by a path connecting the radially inner-most points 152 on each turn of the exterior threading 120. In this embodiment, a core diameter along a first portion 146 of the exterior surface 124 adjacent the head 114 is larger than a core diameter of a second portion 148 of the exterior surface 124 extending from the first portion 146 to the free end 134. Thus, when the nut 106 is fully inserted into the bone so that the head 114 abuts the second side of the bone, the increased core diameter of the first portion 146 provides stability at the cortex where the nut 106 is inserted. Although the first portion 146 of the exterior surface 124 (adjacent the head 114) has a larger core diameter, since the outer contour 150 along the first portion 142 adjacent to the head 114 is reduced, the risk of cracking the cortex when the nut 106 is fully inserted is reduced.

As shown in FIG. 2, although the first portion 142 of the outer contour 150 overlaps with the first portion 146 of the core diameter of the exterior surface 124, a length of the first portion 142 of the outer contour 150 is longer than a length of the first portion 146 of the exterior surface 124. Thus, the nut 106 of this embodiment includes three different threaded portions—threaded portion A which extends along a length of the body 116 corresponding to the length of the second portion 144 of the outer contour 150; a threaded portion B which extends along a length of the body 116 along which the first portion 142 of the outer contour 150 and the second portion 148 of the exterior surface 124 extends; and a threaded portion C which extends along a length of the body portion corresponding to a length of the first portion 146 of the exterior surface 124.

In one embodiment, the length of threaded portion A may range from between approximately 2 mm to 10 mm, the length of threaded portion B may range from between approximately 2 mm to 15 mm, and the length of threaded portion C may range from between approximately 1 mm to 5 mm. The exterior threading 120 extending along the threaded portion A has a depth (i.e., a distance between the radially outermost edges 122 and the core diameter of the exterior surface) that is larger than a depth of the exterior threading 120 along both the threaded portions B and C. The depth of the exterior threading 120 extending along the threaded portion B is smaller than the depth of the exterior threading 120 along the threaded portion A but larger than the depth of the exterior threading 120 along the threaded portion C. Thus, the exterior threading 120 extending along the threaded portion C has the smallest depth relative to the threaded portions A and B.

It will be understood by those of skill in the art that the exterior threading 120 described above may be cut into a wall of a nut, the wall defined via the outer contour 150 and the channel 136 and cut along a trajectory corresponding to the exterior surface 124.

As described above, the system 100 may be used to treat fractures of long bones and, in a particular embodiment, may be used to treat distal fractures of the femur. The intramedullary nail 102 may be inserted through a distal end of the femur so that the distal portion 126 of the intramedullary nail 102 is received within the distal end of the femur and fixed relative thereto via the locking screw 104 inserted through a corresponding locking hole 110, which extends transversely through the distal portion 126 of the nail 102. In one embodiment, the locking screw 104 may be inserted through the first side of the femur so that the shaft 130 extends through the locking hole 110 and the head portion 128 of the locking screw 104 abuts the cortex along the first side of the bone. Although the head portion 128 is described as abutting the bone, it will be understood by those of skill in the art that a washer 112 may be positioned between the head portion 128 and the cortex of the bone.

The nut 106 may then be inserted through the second side of the bone substantially in alignment with the longitudinal axis of the bone screw 104 to engage the free end 118 of the locking screw 104. As the body 116 nut 106 is driven into the bone, the first portion 142 of the outer contour 150 permits slight movements of the nut 106 relative to a longitudinal axis thereof to facilitate alignment of the interior threading 138 along the interior surface 140 of the channel 136 of the nut 106 with the threading 132 of the locking screw 104. The nut 106 may be fully inserted into the bone so that the head 114 of the nut 106 abuts the cortex along the second side of the bone. The increased core diameter along the first portion 146 of the exterior surface 124 provides stability at the cortex when the nut 106 is fully inserted.

The nut 106, however, also prevents cracking at the cortex since the outer contour 150 of the exterior threading 120 along the first portion 142 adjacent the head 114 is smaller than the outer contour along the second portion 144. Although the exemplary embodiment specifically describes and shows use of the system for treating a distal femur, it will be understood by those of skill in the art that the stability and/or compression provided by the locking screw 104 and the nut 106 may be used to treat any of a variety of bones. It will also be understood by those of skill in the art that the intramedullary nail 102, the locking screw 104 and the nut 106 may be inserted/implanted into the bone using any of a variety of methods known in the art.

According to another exemplary embodiment, as shown in FIG. 3, a system 100' comprises a first nut 106a' and a second nut 106b' that may be used to fix both ends of a locking screw 104' to increase nail construct stability. Each of the first and second nuts 106a', 106b' may be substantially similar to the nut 106 of the system 100 and the locking screw 104' may be substantially similar to the locking screw 104 except that the screw 104' does not include a screw head so that both ends of the screw 104' may be received within the nuts 106a' and 106b'. In this embodiment, however, the first nut 106a' is inserted through a cortex along a first side of a bone until a head portion 114' of the first nut 106' contacts the cortex along the first side.

A free end of the locking screw 104' is inserted into the head portion 114' of the first nut 106a' and through a body 116' of the nut 106a' so that a shaft 130' of the locking screw 104' engages a threading along an interior of the body 116'.

The locking screw 104' is moved longitudinally relative to the first nut 106a' until the free end extends beyond the body to engage the bone and a head portion 128' of the locking screw 104' abuts the head portion 114' of the first nut 106a'. In this embodiment, a channel extending through the body 116' of the first nut 106a' may have a larger diameter adjacent the head portion 114' so that the locking screw 104' may more accurately align with an axis of the channel as the locking screw 104' is being inserted into the body 116'.

In other words, slight movement of the locking screw 104' relative to the nut 106a' is permitted during initial insertion of the locking screw 104' to more accurately align the locking screw 104' with the first nut 106a'. Once the locking screw 104' has been inserted through the first nut 106a' and into the bone, as described above, the second nut 106b' may be inserted through a cortex along a second side of the bone opposite the first side to engage the free end of the locking screw 104'. It will be understood by those of skill in the art that insertion of the second nut 106b' to engage the free end 118' may be substantially similar to insertion of the nut 106 as described above with respect to the system 100.

As shown in FIG. 4, a nut 206 according to another exemplary embodiment may be substantially similar to the nut 106 described above with respect to the system 100. Similarly to the nut 106, the nut 206 is configured to engage a free end of a locking screw, which may be substantially similar to the locking screw 104 as described above with respect to the system 100. The nut 206 comprises a head 214 and a body 216 extending longitudinally therefrom to a free end 234. A channel 236 extending longitudinally thereinto from the free end is configured to receive the end of the locking screw therein. Similarly to the nut 106, an outer contour 250 defined via radially outer-most points 222 of an exterior threading 220 extending along an exterior surface 224 of the body 216 includes a first portion 242 adjacent the head 214 and a second portion 244 extending from the first portion 242, the first portion 242 of the outer contour 250 having a diameter smaller than the second portion 244.

Also similarly to the nut 106, the body 216 includes a first portion 246 adjacent the head 214 along which a core diameter along the exterior surface 224 (defined via radially inner-most points 252 of the exterior threading 220) is larger than a core diameter along a second portion 248 extending from the first portion 246. In this embodiment, however, the first portion 242 of the outer contour 250 and the first portion 246 of the exterior surface 224 substantially correspond (e.g., have substantially the same length and extend along the same portion of the body 216) so that threading 220 along the body 216 includes two threaded portions— threaded portion A and threaded portion C—rather than three threaded portions as discussed above with respect to the nut 106.

The threaded portion A extends along a portion of the body 216 corresponding to the second portion 244 of the outer contour 250 and the second portion 248 of the exterior surface 224 while the threaded portion C extends along a portion of the body 216 corresponding to the first portion 242 of the outer contour 250 and the first portion 246 of the exterior surface 224. In one embodiment, a length of the threaded portion A may range between approximately 5 mm and 20 mm and the length of the threaded portion C may range between approximately 1 mm to 20 mm. A depth of the exterior threading 220 along the threaded portion A is larger than a depth of the threading 220 along the threaded portion C. Although the nut 206 only includes two threaded portions A, C, it will be understood by those of skill in the art, that similarly to the nut 106, the reduced diameter of the first portion 242 of the outer contour 250 facilitates alignment with the locking screw (e.g., locking screw 104) as it is being inserted into the bone and the increased diameter of the first portion 246 of the exterior surface 224 facilitates stability at the cortex with cracking the cortex. It will be understood by those of skill in the art that the nut 206 may be used in a manner substantially similar to the nut 106.

It will be understood by those of skill in the art that modifications and variations may be made in the structure and methodology of the present embodiment, without departing from the spirit or the scope of the embodiments. Thus, it is intended that the present embodiments cover the modifications and variations of these embodiments provided that the come within the scope of the appended claims and their equivalents.

What is claimed is:

1. A nut for treating a bone, comprising:
   a head and a body extending longitudinally from the head to a free end and including a channel extending longitudinally thereinto from the free end, the channel configured to engage an end of a bone screw; and
   an exterior threading extending about the body from an exterior surface thereof along an entire length thereof, an outer contour of the exterior threading defined via radially outermost edges of the exterior threading, a first portion of the outer contour adjacent the head portion having a smaller diameter than a second portion of the outer contour extending from the first portion to the free end of the body.

2. The nut of claim 1, wherein a core diameter of a first portion of the exterior surface from which the exterior threading extends is larger than a core diameter of a second portion of the exterior surface extending from the first portion of the exterior surface to the free end of the body.

3. The nut of claim 2, wherein a length of the first portion of the exterior surface is smaller than a length of the first portion of the outer contour.

4. The nut of claim 3, wherein the exterior threading includes three threaded portions, a first threaded portion corresponding to a portion of the exterior threading extending along a length of the body along which the second portion of the outer contour extends, a second threaded portion corresponding to a portion of the exterior threading extending along a length of the body along which the first portion of the outer contour and the second portion of the exterior surface overlap, and a third threaded portion of the exterior threading corresponding to a length of the body along which the first portion of the exterior surface extends.

5. The nut of claim 4, wherein a depth of the exterior threading along the first threaded portion is larger than a depth of the exterior threading along the second threaded portion, which is larger than a depth of the exterior threading along the third threaded portion.

6. The nut of claim 2, wherein a length of the first portion of the outer contour corresponds to a length of the first portion of the exterior surface and a length of the second portion of the outer contour corresponds to a length of the second portion of the exterior surface.

7. The nut of claim 6, wherein the exterior threading includes two threaded portions, a first threaded portion of the exterior threading corresponding to the second portions of the outer contour and the exterior surface and a second threaded portion of the exterior threading corresponding to first portions of the outer contour and the exterior surface.

8. The nut of claim 7, wherein a depth of the exterior threading along the first threaded portion is larger than a depth of the exterior threading along the second threaded portion.

9. The nut of claim 1, further comprising an interior threading extending along an interior surface of the channel for engaging a corresponding threading of the bone screw.

10. A system for treating a long bone, comprising:
an intramedullary nail insertable through a medullary canal of a bone, the intramedullary nail extending from a proximal end to a distal end and including a locking hole extending through the intramedullary nail along an axis extending at an angle relative to a longitudinal axis of the intramedullary nail;
a locking screw configured to be inserted into the bone and through the locking hole, the locking screw including a head portion and a shaft extending therefrom to a free end, the shaft including a threading extending therealong; and
a nut configured to be inserted into bone, the nut including a head and a body extending therefrom to a free end, the body including a channel extending longitudinally thereinto from the free end, the channel configured to threadedly engage the free end of the locking screw, an exterior threading extending about the body from an exterior surface thereof along an entire length thereof, an outer contour of the exterior threading defined via radially outermost edges of the exterior threading, a first portion of the outer contour adjacent the head portion having a smaller diameter than a second portion of the outer contour extending from the first portion to the free end of the body.

11. The system of claim 10, wherein the locking hole extends through a distal portion of the intramedullary nail.

12. The system of claim 10, wherein a core diameter of a first portion of the exterior surface from which the exterior threading extends is larger than a core diameter of a second portion of the exterior surface extending from the first portion of the exterior surface to the free end of the body.

13. The system of claim 12, wherein a length of the first portion of the exterior surface is smaller than a length of the first portion of the outer contour.

14. The system of claim 13, wherein the exterior threading includes three threaded portions, a first threaded portion corresponding to a portion of the exterior threading extending along a length of the body along which the second portion of the outer contour extends, a second threaded portion corresponding to a portion of the exterior threading extending along a length of the body along which the first portion of the outer contour and the second portion of the exterior surface overlap, and a third threaded portion of the exterior threading corresponding to a length of the body along which the first portion of the exterior surface extends.

15. The system of claim 14, wherein a depth of the exterior threading along the first threaded portion is larger than a depth of the exterior threading along the second threaded portion, which is larger than a depth of the exterior threading along the third threaded portion.

16. The system of claim 12, wherein a length of the first portion of the outer contour corresponds to a length of the first portion of the exterior surface and a length of the second portion of the outer contour corresponds to a length of the second portion of the exterior surface.

17. The system of claim 16, wherein the exterior threading includes two threaded portions, a first threaded portion of the exterior threading corresponding to the second portions of the outer contour and the exterior surface and a second threaded portion of the exterior threading corresponding to first portions of the outer contour and the exterior surface.

18. The system of claim 17, wherein a depth of the exterior threading along the first threaded portion is larger than a depth of the exterior threading along the second threaded portion.

19. A method for treating a bone, comprising:
inserting an intramedullary nail into a medullary canal of a femur through an insertion point at a distal end of the femur;
driving a locking screw through a first side of the femur so that a shaft of the locking screw extends through a locking hole extending through a distal portion of the intramedullary nail along an axis angled with respect to a longitudinal axis of the intramedullary nail and a head portion of the locking screw contacts a cortex along the first side of the femur; and
inserting a nut through a second side of the femur opposite the first side of the femur so that a free end of the shaft of the locking screw is threadedly received within a channel of the nut, the nut including a head and a body portion extending from the head to a free end, the channel extending longitudinally into the body from the free end, an exterior threading extending about the body from an exterior surface thereof along an entire length thereof, an outer contour of the exterior threading defined via radially outermost edges of the exterior threading, a first portion of the outer contour adjacent the head portion having a smaller diameter than a second portion of the outer contour extending from the first portion to the free end of the body so that, as the nut is inserted through the bone to engage the locking screw, the nut rotates to align the channel with the threading of the locking screw.

20. The method of claim 19, wherein the nut is fully inserted until the head of the nut contacts a cortex along the second side of the femur to compress the distal end of the bone.

21. The method of claim 20, wherein a core diameter of a first portion of the exterior surface from which the exterior threading extends is larger than a core diameter of a second portion of the exterior surface extending from the first portion of the exterior surface to the free end of the body so that, the nut provides stability at the cortex when fully inserted.

* * * * *